(12) United States Patent
Sakaguchi et al.

(10) Patent No.: US 12,731,672 B2
(45) Date of Patent: Sep. 8, 2026

(54) MEDICAL IMAGE PROCESSING APPARATUS, SYSTEM, AND METHOD

(71) Applicant: CANON KABUSHIKI KAISHA, Tokyo (JP)

(72) Inventors: Takuya Sakaguchi, Utsunomiya (JP); Kazumasa Arakita, Utsunomiya (JP); Hideaki Ishii, Nasushiobara (JP); Takahiko Nishioka, Otawara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 681 days.

(21) Appl. No.: 17/411,473

(22) Filed: Aug. 25, 2021

(65) Prior Publication Data

US 2022/0068468 A1 Mar. 3, 2022

(30) Foreign Application Priority Data

Aug. 25, 2020 (JP) ................................ 2020-141793

(51) Int. Cl.
*G16H 30/40* (2018.01)
*G16H 30/20* (2018.01)
*G16H 50/30* (2018.01)

(52) U.S. Cl.
CPC ............ *G16H 30/40* (2018.01); *G16H 30/20* (2018.01); *G16H 50/30* (2018.01)

(58) Field of Classification Search
CPC ......... G16H 30/40; G16H 30/20; G16H 50/30
USPC .......................................................... 382/128
See application file for complete search history.

(56) References Cited

U.S. PATENT DOCUMENTS 12,207,961 B2 * 1/2025 Liu ........................ A61B 6/504
2010/0312090 A1 * 12/2010 Kerwin ................ G06T 7/0012 382/128
2011/0218427 A1 * 9/2011 Kitamura ............ A61B 6/5217 600/425
2015/0228115 A1 8/2015 Wakai et al.
(Continued)

FOREIGN PATENT DOCUMENTS

JP 2008-534071 A 8/2008
JP 6495037 B2 4/2019
WO WO 2006/102511 A2 9/2006

OTHER PUBLICATIONS

Bishop, "Pattern Recognition and Machine Learning", Springer, (p. 225-290) 2006, 758 pages.
(Continued)

*Primary Examiner* — Michael R Neff
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to acquire a first parameter pertaining to a force at a coronary artery of a subject and a second parameter pertaining to at least one of a shape, character, and fluid resistance related to the coronary artery. The processing circuitry is configured to set, for at least either the first parameter or the second parameter, a weighting factor associated with an anatomical position of the coronary artery. The processing circuitry is configured to calculate, on the basis of the first parameter, the second parameter, and the weighting factor, an index pertaining to a risk on the subject.

19 Claims, 7 Drawing Sheets

(56) References Cited

U.S. PATENT DOCUMENTS

| | | | | |
|---|---|---|---|---|
| 2017/0065484 | A1* | 3/2017 | Addison | A61B 5/7264 |
| 2017/0245821 | A1* | 8/2017 | Itu | G06F 18/2413 |
| 2018/0020998 | A1 | 1/2018 | Wakai et al. | |
| 2018/0085170 | A1* | 3/2018 | Gopinath | A61B 8/0891 |
| 2018/0357767 | A1* | 12/2018 | Arakita | A61B 6/5217 |
| 2020/0205745 | A1* | 7/2020 | Khosousi | G16H 50/70 |

OTHER PUBLICATIONS

Schuijf et al., "Fractional Flow Reserve and Myocardial Perfusion by Computed Tomography: a Guide to Clinical Application", European Society of Cardiology, http://doi.org/10.1093/ehjcl/jex240_2018, 9 pages.

Kate et al. "Fast CT-FFR Analysis Method for the Coronary Artery Based on 4D-CT Image Analysis and Structural and Fluid Analysis", Proceedings of the ASME 2015 International Mechanical Engineering Congress and Exposition IMECE, 2015, 10 pages.

Hirohata et al., "A Novel CT-FFR Method for the Coronary Artery Based on 4D-CT Image Analysis and Structural and Fluid Analysis", Proc. of SPIE vol. 9412, 2015, 15 pages.

* cited by examiner

SUBJECT INFORMATION
SCAN INFORMATION
RECONFIGURA-TION INFORMATION
COMPOSITION
SEGMENT
f
CTP
TERRITORY
FFR
WSS
...
Σ
INDEX
INPUT
CALCULATION
OUTPUT

MEDICAL IMAGE PROCESSING APPARATUS, SYSTEM, AND METHOD

CROSS-REFERENCE TO RELATED APPLICATIONS

This application is based upon and claims the benefit of priority from Japanese Patent Application No. 2020-141793, filed on Aug. 25, 2020; the entire contents of which are incorporated herein by reference.

FIELD

Embodiments disclosed in the present specification and drawings relate generally to a medical image processing apparatus, a system, and a method.

BACKGROUND

Conventionally, there are many patients suffering from ischemic heart disease. Such patients are still increasing in number in this aging society along with increasing lifestyle-related diseases. As indexes used to evaluate a risk of this ischemic heart disease, a shape index, such as stenosis rate, and an index, such as fractional flow reserve (FFR), are known.

DETAILED DESCRIPTION

A medical image processing apparatus according to an embodiment includes processing circuitry. The processing circuitry is configured to acquire a first parameter pertaining to a force at a coronary artery of a subject and a second parameter pertaining to at least one of a shape, character, and fluid resistance related to the coronary artery. The processing circuitry is configured to set, for at least either the first parameter or the second parameter, a weighting factor associated with an anatomical position of the coronary artery. The processing circuitry is configured to calculate, on the basis of the first parameter, the second parameter, and the weighting factor, an index pertaining to a risk on the subject.

Embodiments of a medical image processing apparatus, a system, and a method will now be described herein in detail with reference to the accompanying drawings. Note that the medical image processing apparatus, the system and the method according to the present application are not limited by the embodiments described below. It is possible to combine the embodiments with other embodiments and prior arts within a range where no inconsistency arises in processing contents.

First Embodiment

Figure 1:
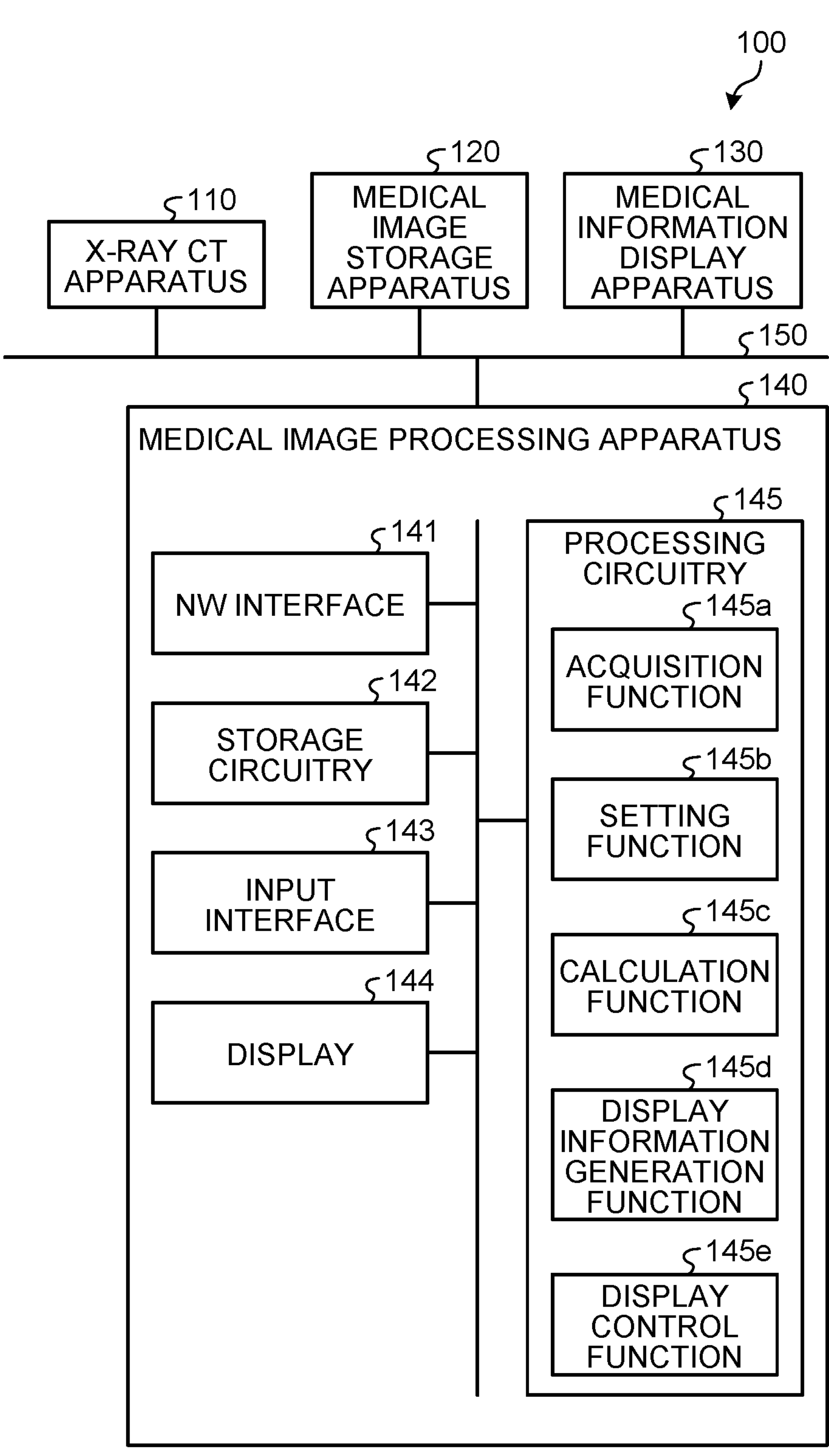
FIG. 1 is a view of a configuration example of a medical image processing system and a medical image processing apparatus according to a first embodiment.

FIG. 1 is a view of a configuration example of a medical image processing system and a medical image processing apparatus according to a first embodiment.

For example, as illustrated in FIG. 1, a medical image processing system 100 according to the present embodiment includes an X-ray computed tomography (CT) apparatus 110, a medical image storage apparatus 120, a medical information display apparatus 130, and a medical image processing apparatus 140. Note herein that the apparatuses and the system are communicably coupled to each other via a network 150.

Note that the medical image processing system 100 may further include, in addition to the X-ray CT apparatus 110, other medical image diagnostic apparatuses such as a magnetic resonance imaging (MRI) apparatus, an ultrasonic diagnostic apparatus, a positron emission tomography (PET) apparatus, and a single photon emission computed tomography (SPECT) apparatus. Furthermore, the medical image processing system 100 may further include other systems such as an electronic health record system, a hospital information system (HIS), and a radiology information system (RIS).

The X-ray CT apparatus 110 is configured to generate a CT image pertaining to a subject. Specifically, the X-ray CT apparatus 110 is configured to cause an X-ray tube and an X-ray detector to rotate and move on a circular orbit surrounding the subject to collect projection data representing the distribution of X-rays passed through the subject. Then, the X-ray CT apparatus 110 generates a CT image on the basis of the collected projection data.

The medical image storage apparatus 120 is configured to store various types of medical images pertaining to the subject. Specifically, the medical image storage apparatus 120 is configured to acquire, via a network 160, a CT image from the X-ray CT apparatus 110, and to cause storage circuitry in the apparatus itself to memorize and store the CT image. For example, the medical image storage apparatus 120 is achieved by using a computer apparatus such as a server and a work station. Furthermore, for example, the medical image storage apparatus 120 is achieved by using a picture archiving and communication system (PACS), and stores a CT image in a format conforming to the digital imaging and communications in medicine (DICOM).

The medical information display apparatus 130 is configured to display various types of medical information pertaining to the subject. Specifically, the medical information display apparatus 130 is configured to acquire, from the medical image storage apparatus 120, via the network 150, medical information such as a CT image and a processing result of image processing, and to cause a display in the apparatus itself to display the medical information. For example, the medical information display apparatus 130 is achieved by using a computer apparatus such as a work station, a personal computer, and a tablet terminal.

The medical image processing apparatus 140 is configured to perform various types of image processing pertaining to the subject. Specifically, the medical image processing apparatus 140 is configured to acquire, from the X-ray CT apparatus 110 or the medical image storage apparatus 120, via the network 150, a CT image, and to use the CT image to perform various types of image processing. Furthermore, the medical image processing apparatus 140 acquires various types of medical information from various types of apparatuses and various types of systems coupled to the medical image processing system 100. For example, the medical image processing apparatus 140 is achieved by using a computer apparatus such as a server and a work station.

For example, the medical image processing apparatus 140 includes a network (NW) interface 141, storage circuitry 142, an input interface 143, a display 144, and processing circuitry 145.

The NW interface 141 is configured to control transmissions and communications of various types of data to be sent and received between the medical image processing apparatus 140 and the other apparatuses and systems being coupled via the network 150. Specifically, the NW interface 141 is coupled to the processing circuitry 145, and is configured to output, to the processing circuitry 145, data received from the other apparatuses and systems or to send data outputted from the processing circuitry 145 to the other apparatuses and systems. For example, the NW interface 141 is achieved by using a network card, a network adapter, and a network interface controller (NIC).

The storage circuitry 142 is configured to store various types of data and various types of computer programs. Specifically, the storage circuitry 142 is coupled to the processing circuitry 145, and is configured to memorize data inputted from the processing circuitry 145 or to read and output memorized data to the processing circuitry 145. For example, the storage circuitry 142 is achieved by using a semiconductor memory element, such as a random access memory (RAM) and a flash memory, a hard disk, and an optical disk.

The input interface 143 is configured to accept input operations of various types of instructions and various types of information from a user. Specifically, the input interface 143 is coupled to the processing circuitry 145, and is configured to convert an input operation received from the user into an electric signal, and to output the electric signal to the processing circuitry 145. For example, the input interface 143 is achieved by using a trackball, switch buttons, a mouse, a keyboard, a touch pad having an operation surface to be touched for an input operation, a touch screen in which a display screen and a touch pad are integrated with each other, a non-contact input interface using an optical sensor, and a voice input interface. Note that, in the present specification, the input interface 143 is not limited to those that include physical operation parts such as a mouse and a keyboard. For example, examples of the input interface 143 include processing circuits for electric signals. The processing circuits are each configured to receive an electric signal corresponding to an input operation, from an external input device provided separately from the present device, and to output the electric signal to a control circuit.

The display 144 is configured to display various types of information and various types of data. Specifically, the display 144 is coupled to the processing circuitry 145, and is configured to display various types of information and various types of data outputted from the processing circuitry 145. For example, the display 144 is achieved by using a liquid crystal display, a cathode ray tube (CRT) display, an organic electro-luminescence (EL) display, a plasma display, or a touch panel.

The processing circuitry 145 is configured to wholly control the medical image processing apparatus 140. For example, the processing circuitry 145 performs various types of processing in accordance with an input operation accepted from the user via the input interface 143. For example, the processing circuitry 145 accepts, via the NW interface 141, data sent from the other apparatuses and systems, and causes the storage circuitry 142 to memorize the accepted data. Furthermore, for example, the processing circuitry 145 outputs, to the NW interface 141, data accepted from the storage circuitry 142 to send the data to the other apparatuses and systems. Furthermore, for example, the processing circuitry 145 causes the display 144 to display data accepted from the storage circuitry 142.

For example, the processing circuitry 145 executes, as illustrated in FIG. 1, an acquisition function 145*a*, a setting function 145*b*, a calculation function 145*c*, a display information generation function 145*d*, and a display control function 145*e*. Note herein that the processing circuitry 145 is an example of processing circuitry.

Note herein that the processing circuitry 145 is achieved by using a processor, for example. In that case, the processing functions described above are memorized in the storage circuitry 142 in the form of computer programs that are executable by a computer. Then, the processing circuitry 145 reads and executes the computer programs memorized in the storage circuitry 142 to achieve the functions corresponding to the computer programs. In other words, the processing circuitry 145 having read the computer programs has the processing functions illustrated in FIG. 1.

Note that the processing circuitry 145 may include a plurality of independent processors in a combined manner. The processors may respectively execute computer programs to achieve the processing functions. The processing functions that the processing circuitry 145 possesses may be achieved appropriately in an integrated manner into a single processing circuit or in a dispersed manner among a plurality of processing circuits. Furthermore, the processing functions that the processing circuitry 145 possesses may be achieved by using a combination of hardware, such as circuits, and software. Furthermore, the example case where the computer programs corresponding to the processing functions are memorized in the single storage circuit 142 has been described in here. However, embodiments are not limited to the example case. For example, the computer programs corresponding to the processing functions may be memorized in a plurality of memory circuits in a dispersed manner. The processing circuitry 145 may be configured to read and execute the computer programs from the memory circuits. The configuration example of the medical image processing system 100 and the medical image processing apparatus 140 according to the present embodiment has been described above. For example, the medical image processing system 100 and the medical image processing apparatus 140 according to the present embodiment are installed in medical facilities such as hospitals and medical offices, and support users such as medical doctors diagnosing heart diseases and designing medical treatment plans.

Note herein that the medical image processing system 100 and the medical image processing apparatus 140 according to the present embodiment use a plurality of indexes that differ in type from each other to provide an index used to evaluate a condition of a subject. Specifically, the medical image processing system 100 and the medical image processing apparatus 140 use indexes that differ in type from each other to provide an index used to evaluate a risk on or benefits for a subject. More specifically, the medical image processing apparatus 140 uses at least two of an index pertaining to shape, an index pertaining to force, an index pertaining to composition (character), and an index pertaining to perfusion (fluid resistance) to calculate an index used to evaluate a risk on a subject or benefits for the subject. That is, the medical image processing apparatus 140 calculates an integrative index using various types of indexes to provide an index for which complex factors are taken into account.

As described above, as indexes used to evaluate a risk of ischemic heart disease, indexes such as stenosis rate and FFR are known. However, practically, a risk of ischemic heart disease relates to various types of factors. That is, the risk of ischemic heart disease is dependent on the factors. Then, the medical image processing apparatus 140 according to the present embodiment provides an index for which the factors are taken into account. Note that the below embodiments describe, as examples, cases when an index used to evaluate a risk on a subject is provided.

Figure 2:
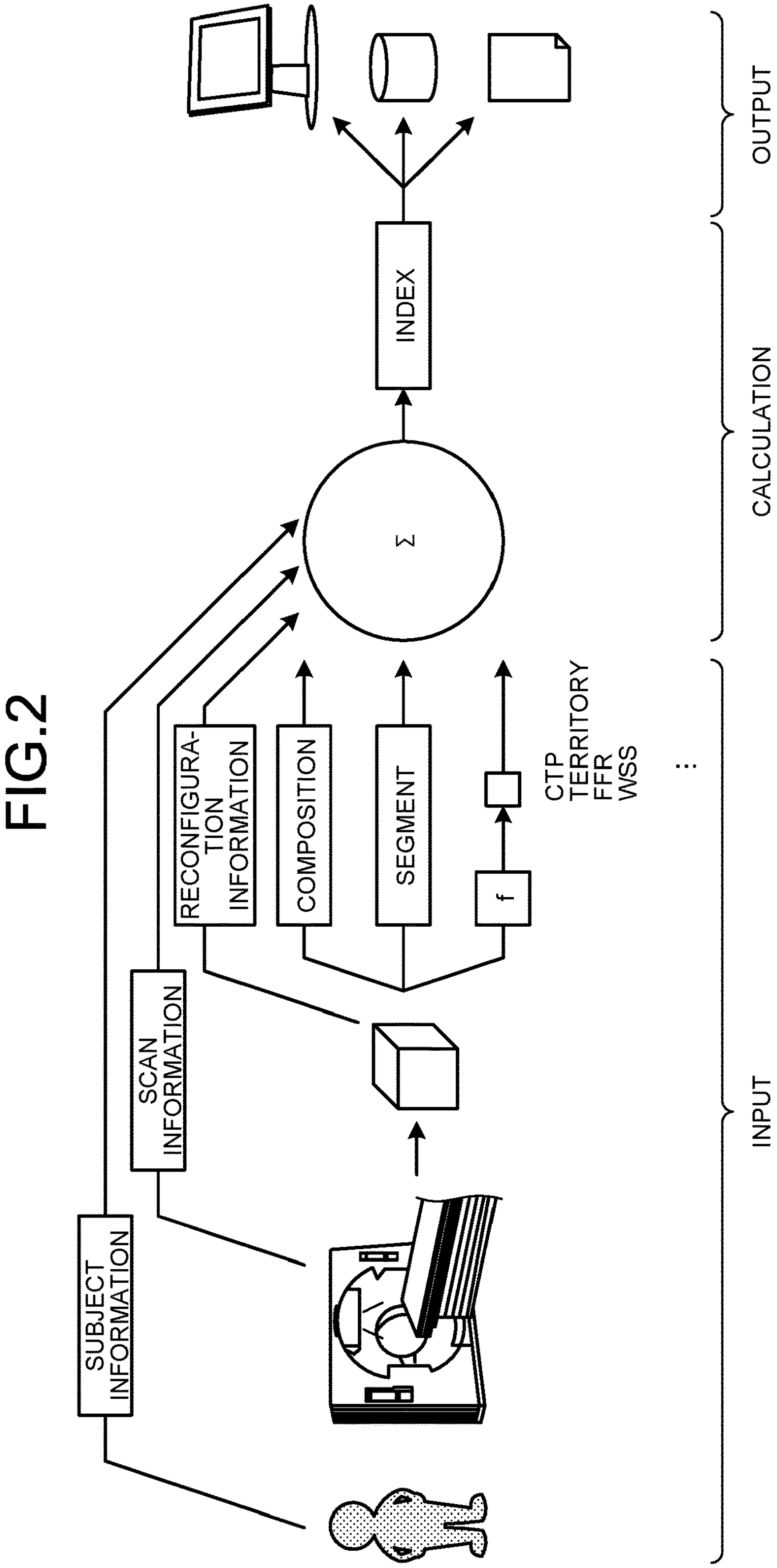
FIG. 2 is a view of an outline of processing performed by the medical image processing apparatus according to the first embodiment.

FIG. 2 is a view of an outline of processing performed by the medical image processing apparatus 140 according to the first embodiment. As illustrated in FIG. 2, the medical image processing apparatus 140 accepts inputs of various types of information pertaining to a subject, calculates a general index "INDEX" used to evaluate a risk on the subject, and outputs the calculated "INDEX" to various types of output destinations.

For example, the medical image processing apparatus 140 acquires, as illustrated in FIG. 2, subject information, scan information, and reconfiguration information. Note herein that the subject information represents information of the attribute and the health history, for example, of the subject. Furthermore, the scan information represents raw data, for example, collected from the subject. Furthermore, the reconfiguration information represents conditions for reconfiguring images, for example.

Furthermore, the medical image processing apparatus 140 acquires, as illustrated in FIG. 2, composition information based on image data (e.g., volume data) generated from the raw data, segment information, and analytical information. Note herein that the composition information represents, for example, information indicative of the character of a coronary artery or a piece of tissue of the myocardium. Furthermore, the segment information represents, for example, information indicative of the shape of a coronary artery or the myocardium. Furthermore, the analytical information represents analytical information pertaining to fluid, such as information of an analytical result pertaining to the blood flow in a coronary artery or of an analytical result of perfusion in the myocardium, for example.

Then, the medical image processing apparatus 140 uses the acquired information to calculate an index used to evaluate a risk on the subject. Specifically, the medical image processing apparatus 140 calculates a general index "INDEX" pertaining to the current condition or prognosis of the subject or pertaining to medical treatment effects. Note herein that, to calculate INDEX, the medical image processing apparatus 140 uses a plurality of indexes that differ in type from each other. Specifically, the medical image processing apparatus 140 uses at least two of an index pertaining to shape, an index pertaining to force, an index pertaining to composition (character), and an index pertaining to perfusion to calculate "INDEX".

That is, the medical image processing apparatus 140 acquires a plurality of indexes in accordance with the type of a general index to be calculated to calculate, from the acquired indexes, the general index "INDEX". Note herein that, the medical image processing apparatus 140 is also able to perform weighting on the indexes used to calculate "INDEX" to calculate a highly precise general index.

Then, the medical image processing apparatus 140 outputs the calculated general index to various types of output destinations. For example, the medical image processing apparatus 140 causes the display 144 to display the calculated general index in one of various types of display forms, causes the calculated general index to be stored in a database, and causes the calculated general index to be outputted in a report.

Details pertaining to inputting information, calculating a general index "INDEX", and outputting the general index "INDEX" will now be described herein. Note that various types of processing examples respectively for inputting information, calculating a general index, and outputting the general index will now be described herein. However, it is possible to combine and implement as desired the processing examples.

Inputting Information

The acquisition function 145*a* is configured to acquire various types of information pertaining to a subject from the other apparatuses and systems coupled to the medical image processing system 100. Specifically, the acquisition function 145*a* is configured to acquire subject information, scan information, reconfiguration information, composition information based on image data, segment information, and analytical information.

For example, the acquisition function 145*a* acquires subject information including the attribute and the health history, for example, of the subject, from the other apparatuses and systems coupled to the medical image processing system 100. Furthermore, for example, the acquisition function 145*a* acquires scan information, reconfiguration information, and image data of the subject from various types of medical image diagnostic apparatuses including the X-ray CT apparatus 110. Furthermore, the acquisition function 145*a* acquires image data of the subject from the medical image storage apparatus 120.

Furthermore, the acquisition function 145*a* acquires composition information based on image data, segment information, and analytical information from various types of medical image diagnostic apparatuses including the X-ray CT apparatus 110 and other apparatuses coupled to the medical image processing system 100. That is, the acquisition function 145*a* acquires information indicative of the character of a coronary artery or a piece of tissue of the myocardium, which is analyzed by the other apparatuses, information indicative of the shape of a coronary artery or the myocardium, which is measured by the other apparatuses, and analytical information pertaining to fluid analyzed by the other apparatuses.

For example, the acquisition function 145*a* acquires, as information indicative of the character of a coronary artery or a piece of tissue of the myocardium, indexes such as calcium score, plaque volume, and the hardness and distribution (cluster) of calcification from the other apparatuses coupled to the medical image processing system 100. Furthermore, for example, the acquisition function 145*a* acquires, as information indicative of the shape of a coronary artery or the myocardium, indexes such as volume, weight, the number of branches, cross-sectional area, diameter, curvature, and stenosis rate (% DS) from the other apparatuses coupled to the medical image processing system 100.

Furthermore, for example, the acquisition function 145*a* acquires, as analytical information pertaining to fluid, indexes pertaining to force and indexes pertaining to perfusion. In an example case, the acquisition function 145*a* acquires, as indexes pertaining to force, indexes such as pressure, FFR, and WSS (wall shear stress) from the other apparatuses coupled to the medical image processing system 100. Furthermore, for example, the acquisition function 145*a* acquires, as indexes pertaining to perfusion, indexes such as CT perfusion (CTP), area (or volume) of perfusion (Territory), and coronary flow reserve (CFR) from the other apparatuses coupled to the medical image processing system 100. Note that the indexes may be calculated on the basis of image data, or may be calculated on the basis of values measured by medical devices (e.g., pressure wire). Note herein that pressure in a blood vessel may be acquired as pressure due to a blood flow at a single point in a blood vessel, for example, or may be acquired as a value acquired by averaging pressure at points within a range across a predetermined length (e.g., approximately 10 mm).

As described above, the acquisition function 145*a* acquires various types of information from the other apparatuses coupled to the medical image processing system 100. However, the acquisition function 145*a* is also able to calculate the indexes described above on the basis of image data. Specifically, the acquisition function 145*a* is able to analyze image data acquired from the various types of medical image diagnostic apparatuses, including the X-ray CT apparatus 110, and the medical image storage apparatus 120 to calculate composition information, segment information, and analytical information.

For example, the acquisition function 145*a* measures, on the basis of image data collected by the medical image diagnostic apparatus including the X-ray CT apparatus 110, indexes such as calcium score, plaque volume, and the distribution and hardness of calcification. Note that measurements for those described above will be executed with known methods using CT values, for example.

Furthermore, for example, the acquisition function 145*a* measures, on the basis of image data collected by the medical image diagnostic apparatus including the X-ray CT apparatus 110, indexes such as volume, weight, the number of branches, cross-sectional area, diameter, curvature, stenosis rate (% DS), and deformation, for a coronary artery or the myocardium. Note that measurements for those described above will be executed with known methods using pixel values and anatomical feature points, for example.

Furthermore, for example, the acquisition function 145*a* calculates, on the basis of image data collected by the medical image diagnostic apparatus including the X-ray CT apparatus 110, indexes such as pressure, FFR, and WSS. Note that calculations of the indexes described above will be executed with known methods using fluid analyses (computational fluid dynamics or CFD) and artificial intelligence (AI), for example.

Furthermore, for example, the acquisition function 145*a* calculates, on the basis of image data collected by the medical image diagnostic apparatus including the X-ray CT apparatus 110, indexes such as CTP, Territory, and CFR. Note that calculations of the indexes described above will be executed with known methods using Perfusion analyses, fluid analyses, and artificial intelligence (AI), for example.

Note that the indexes indicative of character, the indexes indicative of shape, the indexes indicative of force, and the indexes indicative of perfusion, as described above, are mere examples. Other indexes than those described above may be acquired for each type.

As described above, the acquisition function 145*a* is able to acquire subject information, scan information, reconfiguration information, composition information based on image data, segment information, and analytical information. The medical image processing apparatus 140 uses information acquired by the acquisition function 145*a* as inputs to calculate INDEX. Note that acquisitions of information by the acquisition function 145*a* are not limited to a case of acquiring all types of information described above, but may be appropriately and selectively performed in accordance with a general index to be calculated. That is, the acquisition function 145*a* is able to selectively acquire information necessary for a general index to be calculated.

Calculating General Indexes

The calculation function 145*c* is configured to calculate, on the basis of information acquired by the acquisition function 145*a*, an index pertaining to a condition of the subject. Specifically, the calculation function 145*c* is configured to calculate, as an index pertaining to a condition of the subject, the general index "INDEX" used to evaluate a risk on the subject. Specifically, an index using at least two indexes among an index indicative of character, an index indicative of shape, an index indicative of force, . . . and an index indicative of perfusion is calculated as a general index. More specifically, the calculation function 145*c* uses a plurality of indexes determined in accordance with the type of a general index to be calculated to calculate the general index. Note that the calculation function 145*c* is also able to calculate a general index using a weighting factor to be set by the setting function 145*b*, which will be described later in detail.

For example, the calculation function 145*c* uses at least two or more indexes selected from among indexes pertaining to the character of a coronary artery (e.g., calcium score, plaque volume, and distribution and hardness of calcification), indexes pertaining to the shape of a coronary artery and the myocardium (e.g., volume, weight, the number of branches, cross-sectional area, diameter, curvature, and stenosis rate (% DS)), indexes pertaining to a force in a coronary artery (e.g., pressure, FFR, and WSS), and indexes pertaining to perfusion in the myocardium (e.g., CTP, Territory, and CFR) to calculate a general index.

Note herein that, for a general index to be calculated by the calculation function 145*c*, it is sufficient that two or more types of indexes are selected and used, from among the four categories described above (indexes pertaining to character, indexes pertaining to shape, indexes pertaining to force, and indexes pertaining to perfusion). Some indexes may be selected and used, from among indexes belonging to each of the categories. For example, "stenosis rate" may be selected and used, from the indexes indicative of shape, and "FFR" and "WSS" may be selected and used, from the indexes indicative of force, to calculate a general index.

Furthermore, for a general index to be calculated by the calculation function 145*c*, two or more types of indexes are selected and used, from the four categories described above. However, the four categories described above may be classified, and indexes selected from among the classified categories may be selected and used. For example, the four categories may be classified into indexes pertaining to shape to be directly measured from image data (primary index) and indexes pertaining to character, force, and perfusion to be calculated by performing analysis processing on the image data (secondary index). Indexes selected from among the primary index and the secondary index, respectively, may then be used.

Furthermore, a general index to be calculated by the calculation function 145_c_ may be calculated to include indexes pertaining to the coronary arteries and indexes pertaining to the myocardium. Specifically, the calculation function 145_c_ is able to use a functional index for the myocardium to calculate a general index. For example, the calculation function 145_c_ uses "stenosis rate" as an index pertaining to the coronary arteries, and to use "CTP" and "Territory" as indexes pertaining to the myocardium to calculate a general index.

Furthermore, the calculation function 145_c_ is able to further use indexes pertaining to a force generated by a pulsation of the myocardium of the subject to calculate a general index. For example, the calculation function 145_c_ uses a contractile force of the heart of the subject and a force of a movement of a coronary artery due to a pulsation to calculate a general index. In an example case, the acquisition function 145_a_ uses a strain analysis based on image data collected by the medical image diagnostic apparatus including the X-ray CT apparatus 110 to measure an index for the deformation of the myocardium or a coronary artery. The calculation function 145_c_ uses an index for deformation per position, which is calculated by the acquisition function 145_a_, to calculate a general index.

For example, the calculation function 145_c_ uses indexes pertaining to the coronary arteries (shape, character, force, and perfusion), which are acquired by the acquisition function 145_a_, and the indexes pertaining to a force generated by a pulsation of the myocardium to calculate a general index.

The calculation function 145_c_ is able to change indexes to be used in accordance with the type of a general index to be calculated. For example, the calculation function 145_c_ is able to calculate a general index per disease, such as a "general index used to evaluate a risk pertaining to plaque rupture" and a "general index used to evaluate a risk pertaining to ischemia". Furthermore, for example, the calculation function 145_c_ is able to calculate a general index per region (portion), such as a "general index used to evaluate a risk pertaining to blood vessel" and a "general index used to evaluate a risk pertaining to myocardium".

As described above, the calculation function 145_c_ uses a plurality of indexes that differ in type from each other to calculate a general index used to evaluate a risk on the subject. Note herein that the calculation function 145_c_ is able to calculate, in accordance with an input, a general index per pixel, per branch vessel, and per subject. For example, the calculation function 145_c_ is able to use an index calculated per pixel to calculate a general index per pixel (per position). Furthermore, the calculation function 145_c_ is able to use an index value calculated per branch vessel to calculate a general index per branch vessel. Furthermore, the calculation function 145_c_ is able to integrate general indexes calculated at positions in a subject to calculate a general index per the subject.

An example of calculating the general index "INDEX" by the calculation function 145_c_ will now be described herein. For example, the calculation function 145_c_ calculates the general index "INDEX" on the basis of a calculation model illustrated in the below equation (1).

$$\text{INDEX}=f\%(\text{DS},\text{Pressure},\text{FFR},\text{WSS},\text{territory},\text{CFR},\text{calcium score},\text{plaque volume},\text{cluster}) \quad (1)$$

For example, as illustrated in the equation (1), the calculation function 145_c_ calculates a general index with a mathematical function pertaining to "Diameter Stenosis (% DS)", "Pressure", "FFR", "WSS", "Territory", "CFR", "calcium score", "plaque volume", and "cluster".

That is, the calculation function 145_c_ calculates a general index with a mathematical function, as illustrated in the below equation (2), where two or more types of indexes selected from four categories (indexes pertaining to character, indexes pertaining to shape, indexes pertaining to force, and indexes pertaining to perfusion) are indicated as $$\text{INDEX} = f(x) \quad (2)$$

Note herein that the calculation function 145_c_ is able to calculate a general index acquired by multiplying each index by a weighting factor. For example, the calculation function 145_c_ multiplies, as illustrated in the below equation (3), a value "Xi" of each index, by a weighting factor per index "ai", and then perform an addition with the acquired values to calculate the general index "INDEX".

$$\text{INDEX} = \sum (ai * Xi) \quad (3)$$

The weighting factor is set by the setting function 145_b_. The setting function 145_b_ is able to set a weighting factor for each index in accordance with a feature of the index. Specifically, the setting function 145_b_ is configured to set a weighting factor for each index on the basis of a method of acquiring the index, the type of a general index to be calculated, positions of acquiring the indexes, and the types of the indexes, for example.

For example, the setting function 145_b_ sets a weighting factor depending on whether an index corresponds to an index that is to be directly measured from image data (primary index) or an index that is to be calculated by performing analysis processing on image data (secondary index). In an example case, the setting function 145_b_ sets a higher weighting factor for the primary index represented by a numerical value directly acquired from image data, and sets a lower weighting factor, than the weighting factor set for the primary index, for the secondary index for which, for example, a model is used to perform a calculation and a presumption on a numerical value acquired from the image data.

For example, for a CT image, what are to be directly acquired from image data are only indexes pertaining to shape. Then, the setting function 145_b_ sets a further higher weighting factor for an index pertaining to shape (e.g., stenosis rate). Therefore, it is possible to calculate a general index focusing on a value itself directly measured from image data.

Furthermore, for example, the setting function 145_b_ sets a weighting factor for each index in accordance with the type of a general index to be calculated. For example, when a general index is to be calculated per disease, such as a "general index used to evaluate a risk pertaining to plaque rupture" and a "general index used to evaluate a risk pertaining to ischemia", the setting function 145_b_ sets a higher weighting factor for an index for which a causal relation regarded as a disease factor is stronger. Furthermore, for example, when a general index is to be calculated per region (portion), such as a "general index used to evaluate a risk pertaining to blood vessel" and a "general index used to evaluate a risk pertaining to myocardium", the setting function 145*b* sets a higher weighting factor for an index for which a degree of association to the portion is higher.

Furthermore, for example, the setting function 145*b* sets a weighting factor associated with an anatomical position of a coronary artery. That is, the setting function 145*b* is able to set a weighting factor that differs per position.

In an example case, the setting function 145*b* sets, as a weighting factor for FFR, heavier weighting on a proximal side of a coronary artery than weighting on a distal side. That is, the setting function 145*b* increases a weighting factor for FFR on an upstream side of the coronary artery, and decreases a weighting factor for FFR on a downstream side. For example, the setting function 145*b* sets, as a weighting factor to be set for FFR, a weighting factor that gradually decreases from the upstream side to the downstream side.

On the upstream side of a coronary artery, a region controlled by the myocardium is wider. Therefore, when a value of FFR has decreased due to a stenosis, the closer the position of the stenosis is to the upstream side, the greater the impacts to the myocardium. Therefore, by increasing a weighting factor on the upstream side, it is possible to calculate a general index adequately expressing impacts to the whole heart due to a stenosis.

Furthermore, for example, the setting function 145*b* sets, for FFR, a weighting factor proportional to an area of a short axis cross section of a coronary artery. That is, the setting function 145*b* increases a weighting factor for FFR, at a position where an area of a short axis cross section of a coronary artery is wider, and decreases a weighting factor for FFR, at a position where an area of s short axis cross section of the coronary artery is narrower. For example, the setting function 145*b* sets, as a weighting factor to be set for FFR, a weighting factor that gradually decreases as an area of a short axis cross section of a coronary artery decreases.

In the coronary arteries, the wider the cross-sectional area, the more the quantity of blood flow, and the narrower the cross-sectional area, the less the quantity of blood flow. Therefore, impacts to the myocardium when a value of FFR decreases due to a stenosis are significant at a position where a cross-sectional area is wider. Therefore, by increasing a weighting factor as an area of a short axis cross section of the coronary artery increases, it is possible to calculate a general index adequately expressing impacts to the whole heart due to a stenosis.

Furthermore, for example, the setting function 145*b* sets, for FFR, a weighting factor proportional to an area (or volume) of perfusion by a coronary artery. That is, in a coronary artery, the setting function 145*b* increases a weighting factor for FFR at a position where an area (Territory) of supplying blood is wider (a position where an area of the coronary artery supplying blood is wider), and decreases a weighting factor for FFR at a position where an area of supplying blood is narrower (a position where an area of the coronary artery supplying blood is narrower). For example, the setting function 145*b* sets, as a weighting factor to be set for FFR, a weighting factor that gradually decreases as a value of Territory decreases.

When a value of FFR decreases due to a stenosis at a position where an area of supplying blood is wider, there will be greater impacts contributing to the insufficiency of the flow of blood to be supplied to its control region. When a value of FFR decreases due to a stenosis at a position where an area of supplying blood is narrower, there will be less impacts contributing to the insufficiency of the flow of blood to be supplied to its control region. Therefore, by increasing a weighting factor as an area (or volume) of perfusion increases, it is possible to calculate a general index adequately expressing impacts to the whole heart due to a stenosis.

Furthermore, for example, the setting function 145*b* sets, as a weighting factor for FFR, a weighting factor that differs per branch of a coronary artery. In an example case, the setting function 145*b* increases a weighting factor for the left anterior descending coronary artery (LAD), and decreases a weighting factor for the right coronary artery (RCA). Generally, an area (or volume) of perfusion is wider in LAD, and an area (or volume) of perfusion is narrower in RCA. Therefore, by increasing a weighting factor for LAD, it is possible to calculate a general index adequately expressing impacts to the whole heart due to a stenosis.

Furthermore, for example, the setting function 145*b* sets, as a weighting factor for FFR, a weighting factor that differs per segment of a coronary artery. In an example case, in conformance with the American Heart Association (AHA) classification, the setting function 145*b* increases weighting factors for segments numbered at positions adjacent to the proximal side, and decreases weighting factors for segments numbered at positions adjacent to the distal side. That is, since a control region for a segment numbered at a position adjacent to the proximal side is wider, increasing a weighting factor for a segment numbered at a position adjacent to the proximal side makes it possible to calculate a general index adequately expressing impacts to the whole heart due to a stenosis.

Furthermore, for example, the setting function 145*b* sets, as a weighting factor for FFR, a weighting factor that differs in accordance with a position on a coronary artery with respect to the myocardium. In an example case, the setting function 145*b* sets a greater weighting factor for a segment of a coronary artery supplying blood to a part of the myocardium, which corresponds to the left ventricle, than weighting factors for other segments. Since the left ventricle pumps blood for systemic circulation, when a stenosis occurs in a coronary artery supplying blood to a part of the myocardium, which corresponds to the left ventricle, there will be greater impacts to myocardial motions. Therefore, by setting a greater weighting factor for a segment of a coronary artery supplying blood to a part of the myocardium, which corresponds to the left ventricle, than weighting factors for other segments, it is possible to calculate a general index adequately expressing impacts to the whole heart due to a stenosis.

Note that, in the example described above, the setting function 145*b* sets a weighting factor for FFR. However, the setting function 145*b* is able to set weighting factors, respectively, for other indexes pertaining to force, such as WSS and pressure, indexes pertaining to shape, indexes pertaining to character, and indexes pertaining to perfusion.

Furthermore, in the example described above, the setting function 145*b* sets weighting factors, respectively, for indexes pertaining to the coronary arteries. However, the setting function 145*b* is able to similarly set weighting factors, respectively, for indexes pertaining to the myocardium. For example, the setting function 145*b* is able to set, for indexes such as CTP and CFR, weighting factors in accordance with the type of a general index to be calculated and positions of acquiring the indexes, for example.

In an example case, for indexes pertaining to perfusion, such as CTP and CFR, the setting function 145*b* increases weighting factors for a part of the myocardium, which corresponds to the left ventricle, and decreases weighting factors for other parts of the myocardium.

As described above, the setting function 145*b* sets a weighting factor for each index on the basis of a method of acquiring an index, the type of a general index to be calculated, positions of acquiring the indexes, and types of the indexes, for example. Note herein that a weighting factor for each index may be set beforehand per condition and memorized in the storage circuitry 142. The setting function 145*b* may then read and set a weighting factor in accordance with a condition.

Furthermore, the setting function 145*b* may set, for an index, a weighting factor inputted via the input interface 143. In this case, the input interface 143 accepts operations such as an operation of selecting an index for which a weighting factor is to be set and an input operation of inputting a value of a weighting factor for the selected index. The setting function 145*b* sets a weighting factor for each index in accordance with an input operation accepted via the input interface 143. Note that the input interface 143 may accept values of weighting factors one by one, or may accept, as a set, values of a plurality of weighting factors for a plurality of indexes.

For example, to focus on FFR, the user operates the input interface 143 to drastically increase a weighting factor for FFR, and to drastically decrease weighting factors for other indexes. Note herein that, to accept an input operation via the input interface 143, the medical image processing apparatus 140 is able to have a user interface (UI) allowing indexes used to calculate a general index and weighting factors for the indexes to be viewable.

As described above, the calculation function 145*c* is able to use a plurality of indexes that differ in type from each other to calculate a general index. Furthermore, the calculation function 145*c* is able to use the weighting factors for the indexes set by the setting function 145*b* to calculate a general index.

Note herein that the calculation of a general index by the calculation function 145*c* is implemented with the equations (1) to (3) described above, for example. However, such a calculation may be implemented with artificial intelligence (AI). In this case, the value of a general index, which is regarded as the correct value, is first manually specified to a subject for which indexes have been measured. With learning steps, through which a relation between the indexes and the value of the general index is learned, a learned model is then generated.

Note that, for the learning steps described above, it is possible to apply, for example, such a neural network as described in the known non-patent literature ""Pattern recognition and machine learning ", written by Christopher M. Bishop, (USA), First Edition, Springer, 2006, P. 225 to 290". Furthermore, for the learning steps, it is possible to appropriately apply another algorithm than the neural network described above.

Figure 3:
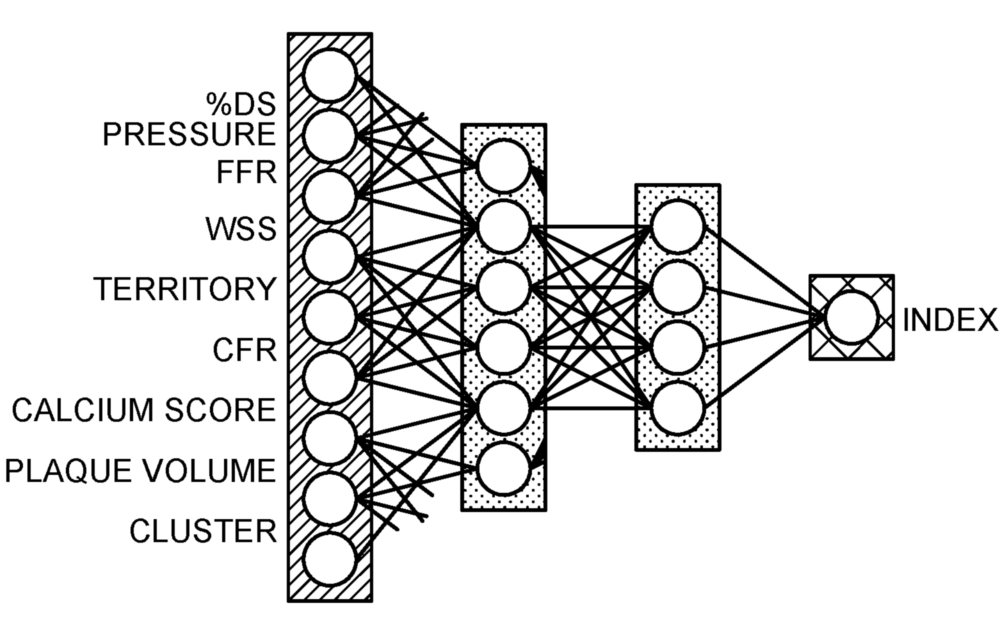
FIG. 3 is a view of an example of how a calculation function according to the first embodiment calculates a general index.

FIG. 3 is a view of an example of how the calculation function 145*c* according to the first embodiment calculates a general index. Note herein that FIG. 3 illustrates a case when a learned model is configured on the basis of a neural network generated by using learning data such as "% DS", "Pressure", "FFR", "WSS", "Territory", "CFR", "calcium score", "plaque volume", and "cluster" and the value of a general index, which is regarded as the correct value. Note that the number of nodes and how edges are coupled to each other, illustrated in FIG. 3, are mere examples. The learned model according to the present embodiment is not limited to the one illustrated in FIG. 3.

For example, the calculation function 145*c* causes values of "% DS", "Pressure", "FFR", "WSS", "Territory", "CFR", "calcium score", "plaque volume", and "cluster" of a subject, which are acquired by the acquisition function 145*a*, to be inputted in the learned model illustrated in FIG. 3 to cause "INDEX" to be outputted from a single output layer.

Note herein that, to calculate "INDEX" through a multiplication with weighting factors, the nodes in the neural network each serve as weighting, for example. In this case, for example, when the UI used to change weighting factors is displayed, it is possible to view the nodes in the neural network. Furthermore, in this case, to facilitate understanding by the user, a neural network may be constructed in such a manner that there are less levels in an intermediate layer of the neural network.

An example of calculating INDEX by the calculation function 145*c* will now be described herein. As described above, the calculation function 145*c* is able to calculate the value of the general index "INDEX" per subject, per branch vessel, per segment of a blood vessel, and per point in an image.

For example, to calculate INDEX per subject, the calculation function 145*c* aggregates calculated INDEX at a plurality of positions to calculate INDEX for the subject. A case of calculating INDEX for the subject by aggregating an index for the left anterior descending coronary artery (LAD), an index for the right coronary artery (RCA), and an index for the left circumflex coronary artery (LCX), in the coronary arteries, will now be described herein.

For example, to aggregate FFR in LAD, FFR in RCA, and FFR in LCX, the calculation function 145*c* aggregates, as illustrated in the below equation (4), values of each branch vessel by multiplying "$FFR_{LAD}$" indicative of FFR in LAD, "$FFR_{RCA}$" indicative of FFR in RCA, and "$FFR_{LCX}$" indicative of FFR in LCX.

$$\mathrm{INDEX} = FFR_{LAD} \times FFR_{RCA} \times FFR_{LCX} \tag{4}$$

Note herein that the calculation function 145*c* is able to use, as values of each branch vessel, values such as average values. However, as illustrated in the below equation (5), it is possible to use a minimum value of FFR in each branch vessel.

$$\mathrm{INDEX} = \min(FFR_{LAD}, FFR_{RCA}, FFR_{LCX}) \tag{5}$$

Then, the calculation function 145*c* uses, as illustrated in the below equation (6), for example, a value of FFR in each branch vessel and a value of an area (or volume) of perfusion "A" in the branch vessel to calculate a general index "INDEX" used to evaluate a risk on the subject. Note that "$A_{LAD}$" in the equation (6) represents an area (or volume) of perfusion in LAD, "$A_{RCA}$" represents an area (or volume) of perfusion in RCA, and "$A_{LCX}$" represents an area (or volume) of perfusion in LCX.

$$\mathrm{INDEX} = (FFR_{LAD} \times A_{LAD}) \times (FFR_{LCX} \times A_{LCX}) \times (FFR_{RCA} \times A_{RCA}) \tag{6}$$

For example, the calculation function 145*c* calculates "INDEX" by multiplying, as illustrated in the equation (6), a multiplied value of "$FFR_{LAD}$" and "$A_{LAD}$", a multiplied value of "$FFR_{LCX}$" and "$A_{LCX}$", and a multiplied value of "$FFR_{RCA}$" and "$A_{RCA}$". Note herein that, to multiply each index by a weighting factor, the calculation function 145*c* multiplies a value of FFR and a value of an area (or volume) of perfusion in each branch vessel, respectively, by weighting factors set in accordance with conditions as described above.

Furthermore, for example, to calculate INDEX per branch vessel, the calculation function 145*c* calculates, as illustrated in the below equation (7), as "$INDEX_{LAD}$" representing a general index for LAD, a multiplied value of "$FFR_{LAD}$" and "$A_{LAD}$". Furthermore, the calculation function 145*c* calculates, as "$INDEX_{LCX}$" representing a general index for LCX, a multiplied value of "$FFR_{LCX}$" and "$A_{LCX}$". Furthermore, the calculation function 145*c* calculates, as "$INDEX_{RCA}$" representing a general index for RCA, a multiplied value of "$FFR_{RCA}$" and "$A_{RCA}$". Note herein that, to multiply each index by a weighting factor, the calculation function 145*c* multiplies a value of FFR and a value of an area (or volume) of perfusion in each branch vessel, respectively, by weighting factors set in accordance with conditions as described above.

$$\mathrm{INDEX}_{LAD} = FFR_{LAD} \times A_{LAD} \qquad (7)$$

$$\mathrm{INDEX}_{LCX} = FFR_{LCX} \times A_{LCX}$$

$$\mathrm{INDEX}_{RCA} = FFR_{RCA} \times A_{RCA}$$

Figure 4:
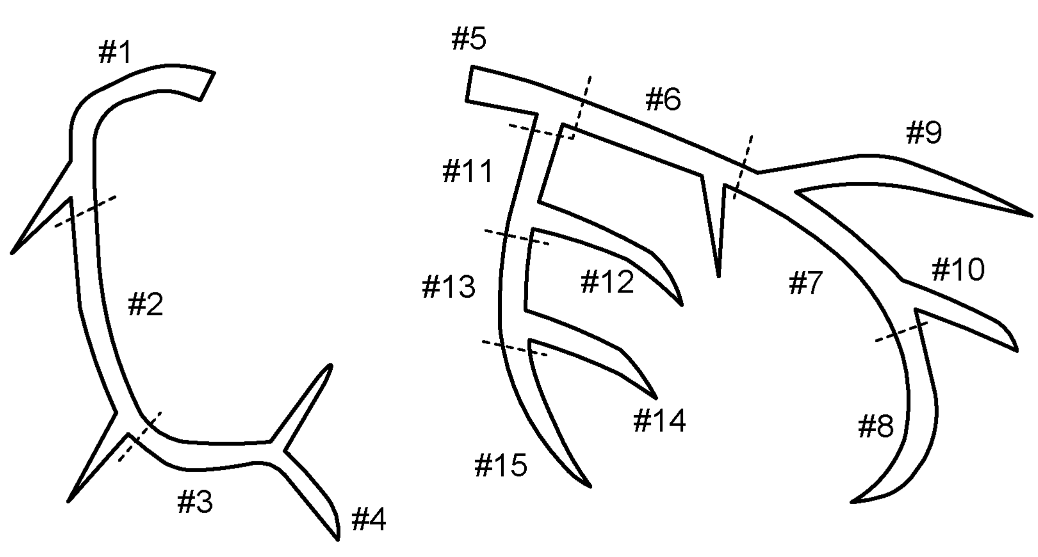
FIG. 4 is a view of an example of segments of blood vessels, according to the first embodiment.

Furthermore, for example, to calculate INDEX per segment of a blood vessel, the calculation function 145*c* calculates, per segment of a blood vessel, a general index using a plurality of indexes that differ in type from each other. FIG. 4 is a view of an example of segments of blood vessels, according to the first embodiment. Note herein that FIG. 4 illustrates segments of the coronary arteries, conforming to the AHA classification. Furthermore, numbers in FIG. 4 represent segment numbers.

For example, the calculation function 145*c* is able to calculate general indexes respectively for the segments illustrated in FIG. 4. In an example case, the calculation function 145*c* calculates, for the segments (#1 to #15), general indexes each acquired by multiplying a representative value of FFR and a value of an area (or volume) of perfusion. Note herein that, to multiply each index by a weighting factor, the calculation function 145*c* multiplies a value of FFR and a value of an area (or volume) of perfusion in each segment, respectively, by weighting factors set in accordance with conditions as described above.

Furthermore, for example, to calculate INDEX per position in an image, the calculation function 145*c* calculates, per pixel, a general index using a plurality of indexes that differ in type from each other. In an example case, the calculation function 145*c* multiplies a value of FFR acquired at a position along a core line of a coronary artery by a weighting factor based on an anatomical position of the coronary artery to calculate a value, multiplies a value of a cross-sectional area at a position along the core line of the coronary artery with a weighting factor based on the area to calculate a value, and further multiplies the value pertaining to FFR and the value pertaining to the cross-sectional area to calculate a general index per position.

Figure 5:
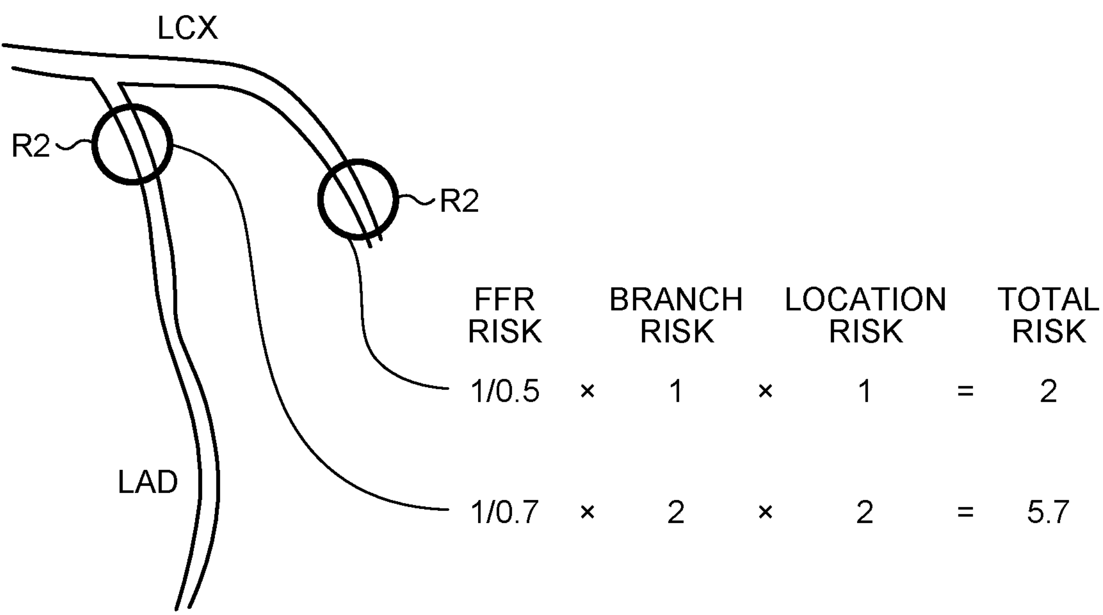
FIG. 5 is a view of an example of how the calculation function according to the first embodiment calculates indexes using weighting factors.

An example of calculating a general index using weighting factors will now be described herein. FIG. 5 is a view of an example of how the calculation function 145*c* according to the first embodiment calculates indexes using weighting factors. Note herein that FIG. 5 illustrates changes in value when FFR is multiplied by a weighting factor. Furthermore, FIG. 5 illustrates values each acquired by multiplying each of a value of FFR in LAD and a value of FFR in LCX by a weighting factor per branch vessel and a weighting factor per position in a blood vessel.

For example, it is assumed in here that the value of FFR in LAD is "0.7" and a value of FFR in LCX is "0.5". In this case, by comparing the values of FFR only, it is evaluated that a risk is higher in LCX. In response to this, the calculation function 145*c* performs a multiplication with, as illustrated in FIG. 5, a weighting factor per branch vessel (Blanch risk) and a weighting factor per position in the blood vessel (Location risk) to calculate a total risk (Total risk).

For example, the calculation function 145*c* multiplies the value of FFR in LCX by "Blanch risk: 1" and "Location risk: 1" to calculate "Total risk: 2". Note that an evaluation takes place in such a manner that the greater the numerical value, the higher the risk. Therefore, the value of FFR uses an inverse number.

Furthermore, the calculation function 145*c* multiplies the value of FFR in LAD by "Blanch risk: 2" and "Location risk: 2" to calculate "Total risk: 5.7". Note herein that LAD has a wider area (or volume) of perfusion, compared with LCX. Therefore, in the calculation example described above, the weighting factor per branch vessel (Blanch risk) is set higher than that for LCX. Furthermore, a position at which the value of FFR in LAD is acquired is closer to the upstream side, compared with LCX. Therefore, in the calculation example described above, the weighting factor per position in the blood vessel (Location risk) is set higher than that for LCX.

As illustrated in FIG. 5, when the weighting factors are used, "Total risk" for LAD is "5.7", the value of which is higher than the value of "Total risk: 2" for LCX. That is, when the weighting factors are used, it is evaluated that the risk is higher in LAD than that in LCX. As described above, by using weighting factors, it is possible to perform different evaluations than those when indexes are only used.

The calculation function 145*c* uses, as illustrated in FIG. 5, weighting factors to perform weighting on an index (FFR in FIG. 5). The calculation function 145*c* is able to similarly multiply other indexes used to calculate a general index, respectively, by weighting factors, and to use the indexes to calculate a general index. Note that it is not necessary to always multiply all indexes used to calculate a general index, respectively, by weighting factors. That is, only some of a plurality of indexes used to calculate a general index may be respectively multiplied by weighting factors.

As described above, the calculation function 145*c* uses a plurality of indexes that differ in type from each other and weighting factors to calculate a general index. Note herein that the calculation function 145*c* is able to change a weighting factor to be used for a multiplication of each index, depending on the type of a general index to be finally outputted. For example, the calculation function 145*c* uses different weighting factors between a case when calculating a general index used to evaluate a risk of myocardial ischemia and a case when calculating a general index used to evaluate a risk in a blood vessel.

In an example case, to perform a medical treatment on a blood vessel, a general index pertaining to a risk on performing a medical treatment on a blood vessel is required to be displayed. In this case, the calculation function 145*c* multiplies a value of a diameter of the blood vessel and a value of the hardness of the blood vessel, respectively, by higher weighting factors. Note herein that indexes for the hardness of a blood vessel include, for example, "calcium score" and "plaque volume".

Furthermore, for example, to perform a medical treatment on the myocardium, a general index pertaining to a risk of performing a medical treatment on the myocardium is required to be displayed. In this case, the calculation function 145*c* multiplies a value of a volume of the myocardium, a value of a percentage of an infarcted region, and a value of an area (or volume) of perfusion, for example, respectively, by higher weighting factors.

As described above, the calculation function 145*c* is able to calculate a general index by changing a weighting factor per the type of a general index to be finally calculated (purposes of the user), per subject, and per the attribute of the subject. Therefore, the calculation function 145*c* allows, for each subject, indexes for a different purpose to be achieved in a single system that operates with a single algorithm with different weighting factors.

For example, to calculate a general index used to evaluate a current state during an acute stage, the calculation function 145*c* calculates a general index by using weighting factors set to perform weighting on a quantity of blood flowing in a blood vessel to calculate the general index. Furthermore, for example, to calculate a general index used to evaluate an ischemia state during a chronic stage, the calculation function 145*c* calculates a general index by using weighting factors set to perform weighting on a quantity of blood flowing to the myocardium to calculate the general index. Furthermore, for example, to calculate a general index used to evaluate a risk of ischemia during a chronic stage, the calculation function 145*c* calculates a general index by using weighting factors set to perform weighting on plaque to output the general index.

In the embodiment described above, a general index is calculated per subject, per branch vessel, per segment of a blood vessel, and per position. However, embodiments are not limited to the embodiment described above. A general index may be calculated per time. In this case, for example, the calculation function 145*c* is able to calculate a general index per cardiac phase (e.g., systolic phase and diastolic phase). In an example case, the calculation function 145*c* uses indexes acquired during the systolic phase to calculate a general index for the systolic phase, and uses indexes acquired during the diastolic phase to calculate a general index for the diastolic phase.

Furthermore, in the embodiment described above, the calculation of a general index for a current state has been described. However, embodiments are not limited to the embodiment described above. A general index after a medical treatment has been performed may be calculated. Specifically, when a medical treatment may change indexes pertaining to shape and blood flow, the calculation function 145*c* is able to use the changed indexes to calculate a general index.

Figure 6:
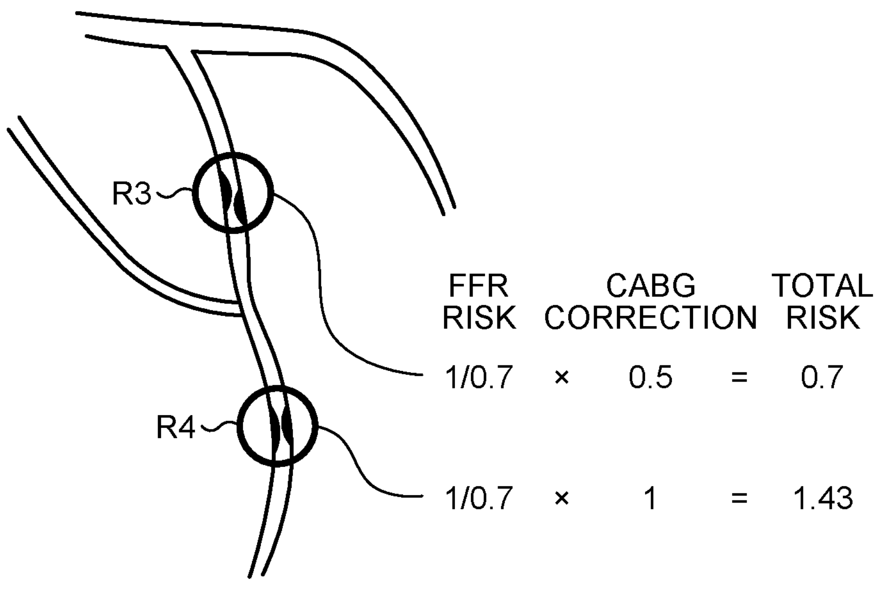
FIG. 6 is a view of an example of how the calculation function according to the first embodiment calculates indexes.

FIG. 6 is a view of an example of how the calculation function according to the first embodiment calculates indexes. Note herein that FIG. 6 illustrates changes when values of FFR are corrected on the basis of a medical treatment. For example, it is assumed in here that a value of FFR in a region R3 lying adjacent to the upstream side of the coronary artery is "0.7", and a value of FFR in a region R4 lying adjacent to the downstream side is "0.7". In this case, by comparing the values of FFR only, it is evaluated that risks are at identical levels in both the region R3 and the region R4. In response to this, as illustrated in FIG. 6, when a bypass is formed between the region R3 and the region R4 through coronary artery bypass grafting (CABG), the calculation function 145*c* applies a correction (CABG correction) due to the bypass.

For example, the calculation function 145*c* multiplies the value of FFR "0.7" in the region R3 by "CABG correction: 0.5" to calculate "Total risk: 0.7". Note herein that blood is supplied downstream of the region R3 due to the bypass. Therefore, a correction is applied to lower a risk of stenosis in the region R3. Furthermore, the calculation function 145*c* multiplies the value of FFR "0.7" in the region R4 by "CABG correction: 1" to calculate "Total risk: 1.43". Note that an evaluation takes place in such a manner that the greater the numerical value, the higher the risk. Therefore, the value of FFR uses an inverse number.

As illustrated in FIG. 6, when a correction is applied due to a medical treatment, "Total risk" of stenosis in the region R3 becomes "0.7", the value of which is lower than "Total risk: 1.43" of stenosis in the region R4. That is, when a correction is applied due to a medical treatment, it is evaluated that a risk of stenosis is lower in the region R3 than a risk of stenosis in the region R4. As described above, by applying a correction due to a medical treatment, it is possible to perform different evaluations than those when indexes are only used.

Note herein that, in FIG. 6, calculating a general index in a state after a medical treatment has been described. However, embodiments are not limited to the embodiment described above. A simulation of medical treatment effects may be performed before a medical treatment. In a case where, for example, a medical treatment may change indexes pertaining to shape and blood flow, when a range for and the content of a medical treatment are inputted, the calculation function 145*c* causes, in accordance with the inputted contents, indexes pertaining to the shape of and a blood flow in a coronary artery to change, and calculates a general index after the changes are made. Therefore, the calculation function 145*c* is able to predictively calculate how a general index fluctuates due to a medical treatment.

For example, in a medical treatment by forming a bypass through placing a stent or CBGA, the shape of a coronary artery is changed in the original data. Furthermore, for example, in a medical treatment through administrating a medicine, a quantity and pressure of blood flowing into a coronary artery are changed from original numerical values. Such changes in index take place for indexes pertaining to a medical treatment to be performed. That is, one or more indexes will be changed in type in accordance with a medical treatment. In a case where, for example, a bypass is formed through CABG, the path of a blood flow is changed, and a quantity of the blood flow is improved by administrating a medicine, the calculation function 145*c* changes a plurality of indexes pertaining to those actions.

Furthermore, by repeating such a simulation as described above while changing little by little the content and a position of a medical treatment, the calculation function 145*c* is also able to determine the content and a position with which a medical treatment brings higher medical treatment effects. In an example case, the calculation function 145*c* changes little by little a position of forming a bypass through CBGA and conditions for administrating a medicine to calculate a general index, respectively. Then, the calculation function 145*c* determines a position of forming a bypass and conditions for administrating a medicine, with which the value of a calculated general index is equal to or below a threshold value. Note that the specified position of forming a bypass and conditions for administrating a medicine may be presented to the user as a medical treatment plan that is deemed to bring higher medical treatment effects.

Furthermore, in the example described above, an optimum medical treatment plan has been determined by changing indexes depending on the content and a position of a medical treatment. However, embodiments are not limited to the embodiment described above. It is possible to calculate a prognosis general index on the basis of changes in index with time passing by. Note that prognosis-related general indexes include, for example, a general index pertaining to quality of life (QOL) and a general index pertaining to major advanced cardiac event (MACE).

For example, the calculation function 145*c* predicts fluctuations of related indexes on the basis of an increase in quantity of blood flow during exertion and hardening of a blood vessel due to aging, and calculates a general index in accordance with the predicted fluctuations. In an example case, the calculation function 145*c* estimates, on the basis of the attribute information of the subject, an increase in quantity of blood flow during exertion and a degree of hardening of a blood vessel due to aging. Then, the calculation function 145*c* predicts fluctuations of related indexes on the basis of the estimated increase in quantity of blood flow during exertion and the estimated degree of the hardening of the blood vessel due to aging. Furthermore, the calculation function 145*c* uses the fluctuated indexes to calculate a general index. Therefore, for example, it is possible to estimate the time when the value of the general index exceeds the threshold value (when a risk emerges).

Furthermore, the calculation function 145*c* is able to determine, from among a plurality of indexes with which a general index has been calculated, an index significantly contributing to a change in the general index. Therefore, the calculation function 145*c* is able to estimate a change in the general index from how the determined index has changed. For example, the calculation function 145*c* determines, on the basis of information of weighting factors, an index significantly contributing to a change in the general index. Then, the calculation function 145*c* estimates, on the basis of the attribute information of a subject, a chronological change in items pertaining to the determined index, and then estimates, from the estimated change, the time when the value of the general index exceeds the threshold value.

In an example case, when FFR is determined as an index significantly contributing to a change in a general index, the calculation function 145*c* estimates a chronological change in items pertaining to FFR (e.g., formation and calcification of plaque) on the basis of the attribute information of the subject. Then, the calculation function 145*c* estimates, from the estimated chronological change in items, the time when the value of the general index exceeds the threshold value.

As described above, the calculation function 145*c* uses a plurality of indexes that differ in type from each other to calculate a general index. Note herein that some examples of general indexes to be calculated by the calculation function 145*c* will now be described herein.

For example, the calculation function 145*c* is able to calculate, as a general index, a ratio of "pressure×cross-sectional area". In an example case, the calculation function 145*c* performs a calculation with "INDEX=(Pd×Δd)/(Pa×Aa)". Note herein that "Pd" represents pressure on the distal side with respect to a pathological change (e.g., stenosis), and "Ad" represents an area of a short axis cross section at a position of "Pd". Furthermore, "Pa" represents pressure on the proximal side with respect to the pathological change (e.g., stenosis), and "Aa" represents an area of a short axis cross section at a position of "Pa".

Furthermore, for example, the calculation function 145*c* is able to calculate, as a general index, a ratio of "pressure× flow quantity". In an example case, the calculation function 145*c* performs a calculation with "INDEX=(Pd×Q)/(Pa×Q)". Note herein that "Q" represents a flow quantity.

Furthermore, for example, the calculation function 145*c* is able to calculate, as a general index, a ratio of "pressure/flow quantity". In an example case, the calculation function 145*c* performs a calculation with "INDEX=(Pd/Q)/(Pa/Q)".

Furthermore, for example, the calculation function 145*c* is able to calculate, as a general index, a ratio of pressure, as illustrated in the below equation (8). Note herein that "iFR" in the equation (8) represents FFR during a resting state. Furthermore, "$P_m$" in the equation (8) represents pressure at a measurement point, "$P_0$" represents static pressure, "$P_d$" represents pressure on the distal side with respect to a pathological change (e.g., stenosis), and "$P_a$" represents pressure on the proximal side with respect to the pathological change (e.g., stenosis).

$$\text{INDEX} = FFR \times \frac{iFR}{iFR_{distal}} = \frac{P_m - P_0}{P_a - P_0} \times \frac{P_m/P_a}{P_d/P_a} \tag{8}$$

Furthermore, for example, the calculation function 145*c* is able to use pressure and a CT value on a core line as illustrated in the below equation (9) to calculate a general index. Note herein that "$P_m$" in the equation (9) represents pressure at a measurement point, "Pa" represents pressure on the proximal side with respect to a pathological change (e.g., stenosis), "$TAG_m$" represents a CT value at a position on a core line, corresponding to the measurement point, and "$TAG_a$" represents a CT value at a position on the core line, corresponding to the position at which "Pa" is measured.

$$\text{INDEX} = \frac{P_m \times \text{TAG}_m}{P_a \times \text{TAG}_a} \tag{9}$$

How the calculation function 145*c* calculates a general index has been described above. A general index calculated by the calculation function 145*c* will be outputted in one of various types of forms.

Outputting General Index

The display information generation function 145*d* is configured to generate various types of information for display purposes. Specifically, the display information generation function 145*d* is configured to generate images for display purposes and reference information used to refer to a general index. For example, the display information generation function 145*d* three-dimensionally reconfigures a blood vessel region of a coronary artery in a CT image of the coronary artery to generate a three-dimensional image of the coronary artery. For example, the display information generation function 145*d* generates virtual reality (VR) images, surface rendering (SR) images, curved planer reconstruction (CPR) images, multi-planer reconstruction (MPR) images, and stretched multi-planer reconstruction (SPR) images.

Furthermore, for example, the display information generation function 145*d* generates, as reference information used to refer to a general index, a map reflecting values of indexes included in the general index. In an example case, the display information generation function 145*d* generates a two-dimensional map reflecting values of indexes included in a general index.

The display control function 145*e* is configured to cause the display 144 to display various types of information for display purposes generated by the display information generation function 145*d*. Specifically, the display control function 145*e* is configured to cause the display 144 to display images for display purposes and reference information used to refer to a general index.

Figure 7A:
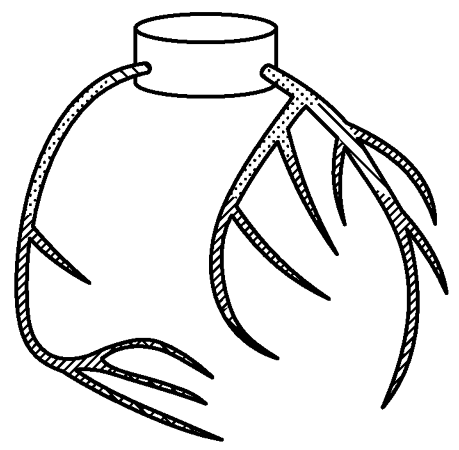
FIG. 7A is a view of a display example by a display control function according to the first embodiment.
Figure 7B:
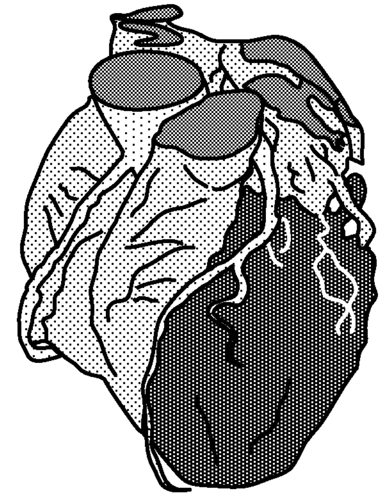
FIG. 7B is a view of a display example by the display control function according to the first embodiment.

For example, the display control function 145*e* causes an image of the spatial distribution of a general index calculated by the calculation function 145*c* to be displayed. FIGS. 7A and 7B are views each illustrating a display example by the display control function 145*e* according to the first embodiment.

For example, as illustrated in FIG. 7A, the display control function 145*e* causes a color image of positions of the coronary arteries to be displayed in colors in accordance with values of general indexes calculated at the positions of the coronary arteries. Furthermore, for example, as illustrated in FIG. 7B, the display control function 145*e* causes a color image of positions of the myocardium to be displayed in colors in accordance with values of general indexes calculated at the positions of the myocardium.

Furthermore, the display control function 145*e* causes a map to be displayed, the map reflecting values of indexes included in a general index, as reference information used to refer to the general index. For example, the display control function 145*e* causes a two-dimensional map to be displayed, where a horizontal axis indicates a first parameter and a vertical axis indicates a second parameter.

Figure 8:
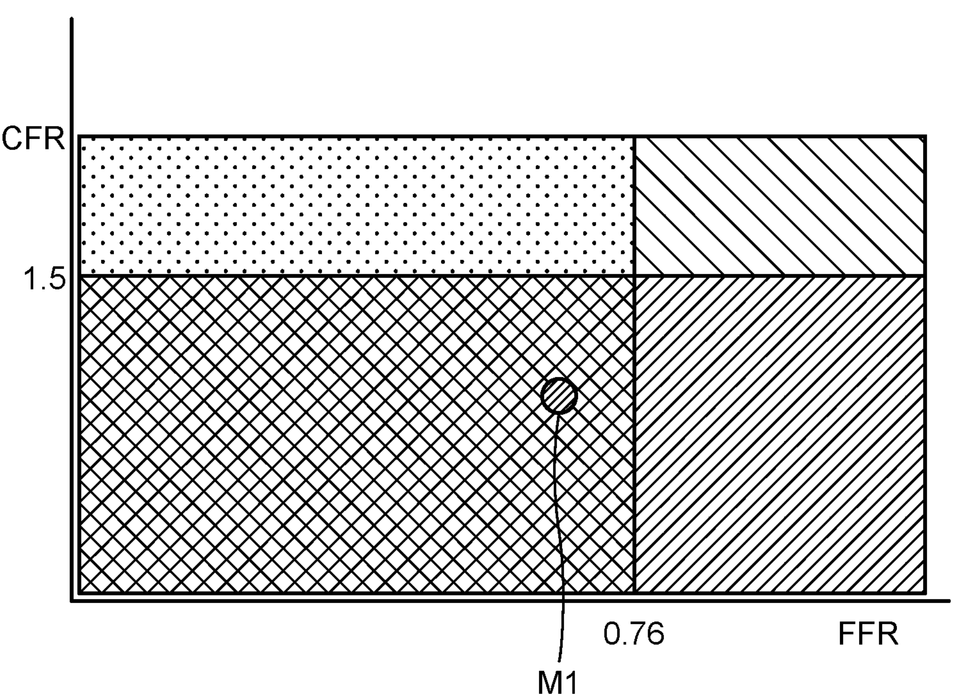
FIG. 8 is a view of a display example by the display control function according to the first embodiment.

FIG. 8 is a view of a display example by the display control function 145*e* according to the first embodiment. For example, as illustrated in FIG. 8, the display control function 145*e* causes a color map to be displayed, where a horizontal axis indicates FFR, and a vertical axis indicates CFR, and the graph of which is colored in accordance with the value of a general index. Note herein that, for example, when only two types of indexes are used to calculate a general index, the display control function 145*e* causes a color map to be displayed, the graph of which is colored only in accordance with the value of the general index.

On the other hand, when three or more types of indexes are used to calculate a general index, the display control function 145*e* causes a two-dimensional map to be displayed, where, among indexes used to calculate the general index, two indexes with higher weighting factors are indicated on the vertical axis and the horizontal axis. Then, the display control function 145*e* causes a color map to be displayed, the map reflecting values of the other indexes than the indexes indicated on the vertical axis and the horizontal axis.

For example, when a general index is calculated by using three types of indexes, and information is displayed in the color map illustrated in FIG. 8, the display control function 145*e* allocates, for four sections separated in accordance with the values of FFR and CFR, colors in accordance with the value of the general index. Furthermore, the display control function 145*e* applies gradations in accordance with a value of a third index to the four sections, making it possible to identify the value of the third index.

Note that FIG. 8 illustrates a case when a graph is separated into four sections, and the four sections are colored in accordance with the value of the general index. However, embodiments are not limited to the embodiment described above. A graph may be separated into five or more sections. Furthermore, a graph may be separated by not only straight lines, but also curved lines in accordance with a relation between the value of a general index and the value of an index indicated by the vertical axis and the value of an index indicated by the horizontal axis.

Furthermore, the display control function 145*e* is able to cause the images illustrated in FIGS. 7A and 7B and the map illustrated in FIG. 8 to be displayed in a linked manner. For example, as illustrated in FIG. 8, the display control function 145*e* causes a marker M1 to be displayed at a position on the map, which corresponds to a position specified in the image. Furthermore, the display control function 145*e* is able to cause the value of a general index and the values of indexes used to calculate the general index to be displayed, together with the marker M1.

Figure 9:
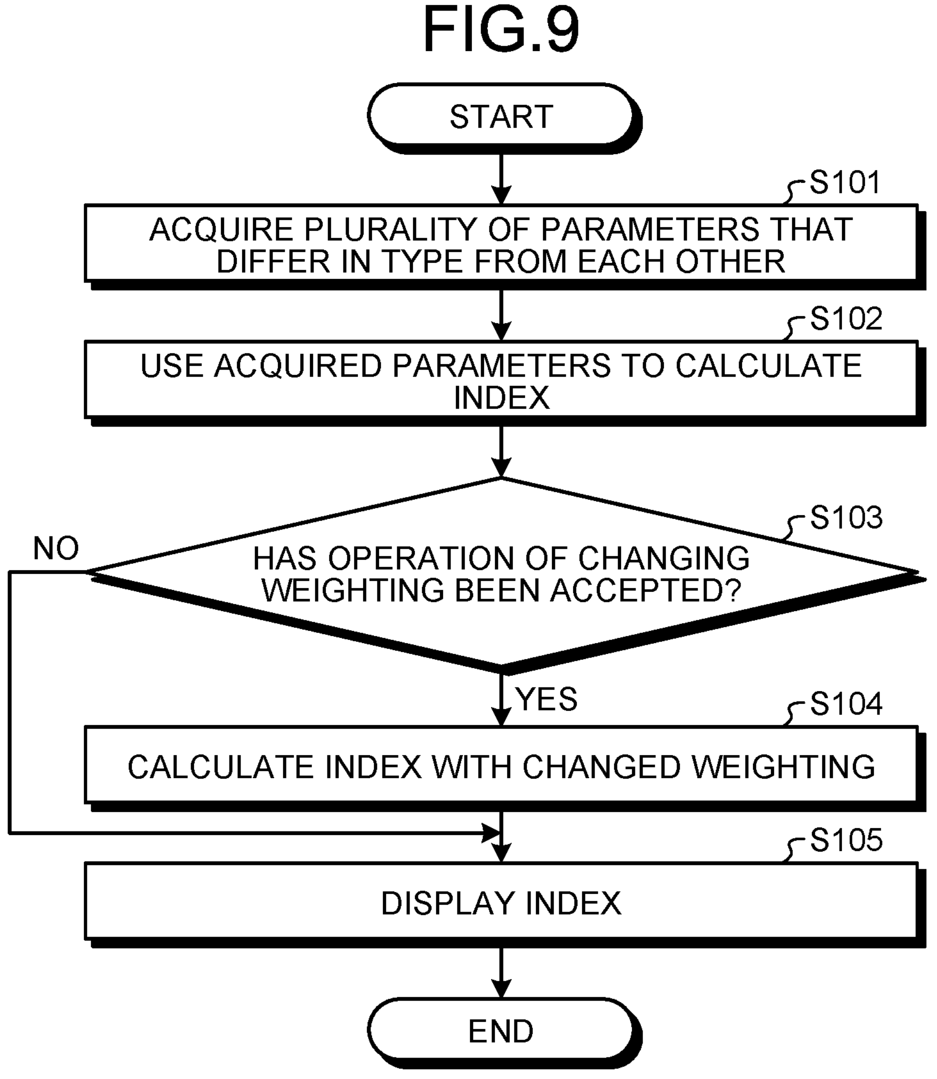
FIG. 9 is a flowchart of a processing procedure of processing performed by processing functions that processing circuitry of the medical image processing apparatus according to the first embodiment possesses.

Next, a processing procedure of the medical image processing apparatus 140 will now be described herein with reference to FIG. 9. FIG. 9 is a flowchart of a processing procedure of processing performed by the processing functions that the processing circuitry 145 of the medical image processing apparatus 140 according to the first embodiment possesses.

For example, as illustrated in FIG. 9, upon the acceptance of an instruction of starting the processing from the user via the input interface 143, the acquisition function 145*a* acquires a plurality of parameters (indexes) that differ in type from each other from the other apparatuses and systems coupled to the medical image processing system 100 (step S101). Note herein that the acquisition function 145*a* is also able to acquire parameters (indexes) by calculating the parameters (indexes) from acquired image data. The processing is achieved, for example, when the processing circuitry 145 calls and executes a computer program corresponding to the acquisition function 145*a* from the storage circuitry 142.

Next, the calculation function 145*c* uses the parameters acquired by the acquisition function 145*a* to calculate "INDEX" (step S102). Then, the calculation function 145*c* determines whether an operation of changing a weighting factor is accepted (step S103). Note herein that when the change operation is accepted (positive at step S103), the calculation function 145*c* calculates "INDEX" with the changed weighting factor (step S104). The processing is achieved, for example, when the processing circuitry 145 calls and executes a computer program corresponding to the calculation function 145*c* from the storage circuitry 142.

Next, the display control function 145*e* causes "INDEX" calculated at step S102 or step S104 to be displayed (step S105). The processing is achieved, for example, when the processing circuitry 145 calls and executes a computer program corresponding to the display control function 145*e* from the storage circuitry 142.

As described above, according to the first embodiment, the acquisition function 145*a* acquires a first parameter pertaining to fluid in a coronary artery of a subject and a second parameter pertaining to at least one of the shape or character of the coronary artery. The setting function 145*b* sets, for at least either the first parameter or the second parameter, a weighting factor associated with an anatomical position of the coronary artery. The calculation function 145*c* calculates, on the basis of the first parameter, the second parameter, and the weighting factor, an index pertaining to a risk on the subject. Therefore, the medical image processing apparatus 140 according to the first embodiment is able to calculate a general index adequately expressing impacts to the heart, making it possible to improve the accuracy of a risk evaluation.

Furthermore, according to the first embodiment, the acquisition function 145*a* acquires, as the first parameter, FFR acquired on the basis of an image of a coronary artery of the subject. Therefore, the medical image processing apparatus 140 is able to calculate a general index by combining, in addition to FFR, the shape and character of a coronary artery, making it possible to improve the accuracy of a risk evaluation.

Furthermore, according to the first embodiment, the setting function 145*b* sets, as a weighting factor for FFR, heavier weighting on the proximal side of a coronary artery than weighting on the distal side. Therefore, the medical image processing apparatus 140 according to the first embodiment is able to set a weighting factor making weighting heavier at a position where a control region is wider, making it possible to calculate a general index adequately expressing impacts to the heart.

Furthermore, according to the first embodiment, the setting function 145*b* sets, for FFR, a weighting factor proportional to an area of a short axis cross section of a coronary artery. Therefore, the medical image processing apparatus 140 according to the first embodiment is able to increase a weighting factor for a position where a quantity of blood flow is greater, making it possible to calculate a general index adequately expressing impacts to the heart.

Furthermore, according to the first embodiment, the setting function 145*b* sets, for FFR, a weighting factor proportional to an area (or volume) of perfusion by a coronary artery. Therefore, the medical image processing apparatus 140 according to the first embodiment is able to increase a weighting factor for a position where impacts due to a decrease in quantity of blood flow are greater, making it possible to calculate a general index adequately expressing impacts to the heart.

Furthermore, according to the first embodiment, the setting function 145*b* sets, as a weighting factor for FFR, a weighting factor that differs per branch of a coronary artery. Therefore, the medical image processing apparatus 140 according to the first embodiment is able to set a weighting factor in accordance with an area (or volume) of perfusion, making it possible to calculate a general index adequately expressing impacts to the heart.

Furthermore, according to the first embodiment, the acquisition function 145*a* further acquires a third parameter pertaining to the myocardium of the subject. The calculation function 145*c* calculates, on the basis of the first parameter, the second parameter, the weighting factor, and the third parameter, an index pertaining to a risk on the subject. Therefore, the medical image processing apparatus 140 according to the first embodiment is able to calculate a general index including indexes pertaining to the coronary arteries and indexes pertaining to the myocardium, making it possible to calculate a general index adequately expressing impacts to the heart.

Furthermore, according to the first embodiment, the setting function 145*b* further sets, for the third parameter, weighting associated with an anatomical position of the myocardium. Therefore, the medical image processing apparatus 140 according to the first embodiment makes it possible to more adequately express impacts to the heart.

Furthermore, according to the first embodiment, the acquisition function 145*a* further acquires a fourth parameter pertaining to a force generated by a pulsation of the myocardium of the subject. The calculation function 145*c* further uses the fourth parameter to calculate an index pertaining to a risk on the subject. Therefore, the medical image processing apparatus 140 according to the first embodiment is able to calculate a general index including indexes pertaining to the coronary arteries and indexes pertaining to a force generated by a pulsation of the myocardium, making it possible to calculate a general index adequately expressing impacts to the heart.

Furthermore, according to the first embodiment, the display control function 145*e* causes an image of the spatial distribution of an index calculated by the calculation function 145*c* to be displayed. Therefore, the medical image processing apparatus 140 according to the first embodiment makes it possible to cause the distribution of a general index to be displayed in an easily observable manner.

Furthermore, according to the first embodiment, the display control function 145*e* causes a map to be displayed, the map reflecting a value of the first parameter and a value of the second parameter included in an index calculated by the calculation function 145*c*. Therefore, the medical image processing apparatus 140 according to the first embodiment makes it possible to simultaneously observe a general index and indexes used for calculations.

Furthermore, according to the first embodiment, the acquisition function 145*a* acquires a first parameter pertaining to a coronary artery of a subject and a second parameter pertaining to the myocardium or a pulsation of the myocardium of the subject. The setting function 145*b* sets, for at least either the first parameter or the second parameter, a weighting factor associated with an anatomical position of a coronary artery. The calculation function 145*c* calculates, on the basis of the first parameter, the second parameter, and the weighting factor, an index pertaining to a risk on the subject. Therefore, the medical image processing apparatus 140 according to the first embodiment is able to calculate a general index adequately expressing impacts to the heart, making it possible to improve the accuracy of a risk evaluation.

Other Embodiments

In the embodiment described above, as an index pertaining to a condition of a subject, a general index "INDEX" used to evaluate a risk is calculated, and the calculated "INDEX" is outputted. However, embodiments are not limited to the embodiment described above. As an index pertaining to a condition of a subject, a general index "INDEX" used to evaluate benefits for the subject may be calculated, and the calculated "INDEX" may be outputted.

In this case, the calculation function 145*c* according to the other embodiments calculates, as an index pertaining to the condition of the subject, an index pertaining to benefits for the subject. Note herein that the calculation function 145*c* calculates, as the general index "INDEX" used to evaluate benefits for the subject, for example, an inverse number of the general index "INDEX" described in the first embodiment.

For example, the calculation function 145*c* calculates "INDEX" used to evaluate benefits in a simulation of medical treatment effects and "INDEX" used to evaluate prognosis benefits. In an example case, the calculation function 145*c* calculates, on the basis of a plurality of indexes, a general index "INDEX" pertaining to medical treatment effects. Therefore, in medical treatments pertaining to a plurality of indexes included in the general index "INDEX", it is possible to acquire, through a simulation, a more effective medical treatment (that improves INDEX).

Furthermore, for example, the calculation function 145*c* calculates, on the basis of a plurality of indexes, "INDEX" pertaining to survival rate after a certain period (e.g., immediately after medical treatment, five hours, and five years), "INDEX" pertaining to QOL, "INDEX" pertaining to MACE, and "INDEX" pertaining to treatment success rate.

With the general index "INDEX", finding an index contributing to make better the general index "INDEX" makes it possible to determine a treatment (medical treatment) for increasing a survival rate, a treatment (medical treatment) for increasing QOL, a treatment (medical treatment) for decreasing an incidence rate of MACE, and a treatment (medical treatment) for increasing a treatment success rate, for example.

In the embodiments described above, the display 144 of the medical image processing apparatus 140 is caused to display information pertaining to a general index. However, embodiments are not limited to the embodiments described above. For example, a display of the medical information display apparatus 130 may be caused to display information pertaining to a general index.

In the embodiments described above, an acquisition part, a setting part, a calculation part, and a display control part in the present specification are respectively achieved with the acquisition function, the setting function, the calculation function, and the display control function of the processing circuitry. However, embodiments are not limited to the embodiments described above. For example, in addition to achieving the acquisition part, the setting part, the calculation part, and the display control part in the present specification with the acquisition function, the setting function, the calculation function, and the display control function described in the above embodiments, the parts may be achieved with hardware only, software only, or a combination of hardware and software.

The term "processor" described in the above embodiments means, for example, a circuit including a central processing unit (CPU), a graphics processing unit (GPU), an application specific integrated circuit (ASIC), and a programmable logic device (e.g., a simple programmable logic device (SPLD), a complex programmable logic device (CPLD), and a field programmable gate array (FPGA)). Note that, instead of storing computer programs in the storage circuitry, such a configuration may be applied that computer programs are directly incorporated in a circuit in a processor. In this case, the processor reads and executes the computer programs incorporated in the circuit to achieve the functions. The processor according to the present embodiments is not limited to one where the processor is configured as a single circuit. However, a plurality of independent circuits may be combined to configure a single processor to achieve the functions.

Note herein that the computer programs executed by the processor are provided in such a manner that the computer programs are incorporated beforehand in a storage circuit such as a read only memory (ROM). Note that the computer programs may otherwise be provided in such a manner that the computer programs in the form of files in a format installable to the devices or in an executable format are recorded in a computer-readable, non-transitory storage medium such as a compact disc-read only memory (CD-ROM), a flexible disk (FD), a compact disc-recordable (CD-R), or a digital versatile disc (DVD). The computer programs may be stored on a computer coupled to a network such as the Internet, downloaded via the network, and provided or distributed. For example, the computer programs each include modules serving as the processing functions as described above. In actual hardware, as a CPU reads, from a storage medium such as a ROM, and executes each of the computer programs, the modules are loaded on a main memory device, and then generated on the main memory device.

Furthermore, in the above described embodiments and modification examples, the components of the apparatuses are functionally and schematically illustrated, and may not be necessarily physically configured as illustrated. That is, a specific, dispersed or integrated form of the apparatuses is not limited to the forms illustrated in the embodiments. The apparatuses may be wholly or partially and functionally or physically configured in a dispersed or integrated manner in terms of a desired unit in accordance with various kinds of loads and use situations, for example. Furthermore, the processing functions implemented in the apparatuses may be wholly or partially achieved as desired through a CPU and a computer program analyzed and executed by the CPU, or achieved as wired logic hardware.

Furthermore, among the steps of the processing described above in the embodiments and modification examples, it is possible to execute manually some or all of the steps of the processing that has been described to be executed automatically. Otherwise, it is possible to execute automatically, with a known method, some or all of the steps of the processing that has been described to be executed manually. In addition, unless otherwise specifically described, it is possible to alter as desired the steps of processing and controls, specific names, and information including various types of data and parameters described above in the specification and the accompanying drawings.

According to at least one of the embodiments described above, it is possible to improve the accuracy of a risk index.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:

processing circuitry configured to:

acquire a first parameter pertaining to a fractional flow reserve of a coronary artery of a subject and a second parameter pertaining to at least one of a shape, character, and fluid resistance related to the coronary artery;

set a weighting factor for the coronary artery, wherein a heavier value is set for the weighting factor at a proximal side than the weighting factor at a distal side; and calculate, based on the first parameter, the second parameter, and the weighting factor, an index pertaining to a condition of the subject.

2. The medical image processing apparatus according to claim 1, wherein the processing circuitry is configured to acquire, as the first parameter, a pertaining to the fractional flow reserve acquired based on an image of the coronary artery of the subject.

3. The medical image processing apparatus according to claim 1, wherein the processing circuitry is configured to reset the weighting factor to a weighting factor proportional to an area of a short axis cross section of the coronary artery.

4. The medical image processing apparatus according to claim 1, wherein the processing circuitry is configured to reset the weighting factor to a weighting factor proportional to an area or volume of perfusion by the coronary artery.

5. The medical image processing apparatus according to claim 1, wherein the processing circuitry is configured to reset the weighting factor to a weighting factor that differs per branch of the coronary artery.

6. The medical image processing apparatus according to claim 1, wherein the processing circuitry is configured to:

further acquire a third parameter pertaining to a myocardium of the subject; and calculate, based on the first parameter, the second parameter, the weighting factor, and the third parameter, an index pertaining to a condition of the subject.

7. The medical image processing apparatus according to claim 6, wherein the processing circuitry is configured to further set, for the third parameter, weighting associated with an anatomical position of the myocardium.

8. The medical image processing apparatus according to claim 1, wherein the processing circuitry is configured to:

further acquire a fourth parameter pertaining to a force generated by a pulsation of a myocardium of the subject; and further use the fourth parameter to calculate an index pertaining to a condition of the subject.

9. The medical image processing apparatus according to claim 1, wherein the processing circuitry is configured to cause an image of spatial distribution of the index to be displayed.

10. The medical image processing apparatus according to claim 1, wherein the processing circuitry is configured to cause a map to be displayed, the map reflecting a value of the first parameter and a value of the second parameter included in the index.

11. The medical image processing apparatus according to claim 1, wherein the processing circuitry is configured to calculate, as an index pertaining to a condition of the subject, an index pertaining to a risk on the subject.

12. The medical image processing apparatus according to claim 1, wherein the processing circuitry is configured to calculate, as an index pertaining to a condition of the subject, an index pertaining to benefits for the subject.

13. A medical image processing system comprising:

the medical image processing apparatus according to claim 1; and a medical information display apparatus.

14. The medical image processing apparatus according to claim 1, wherein the fractional flow reserve is calculated at two or more different positions along a longitudinal axis of the coronary artery.

15. The medical image processing apparatus according to claim 1, wherein the processing circuitry is configured to cause a display to display the first parameter, the second parameter, and the weighting factor.

16. The medical image processing apparatus according to claim 1, wherein the processing circuitry is configured to reset the weighting factor to a weighting factor pertaining to an area of a short axis cross section of the coronary artery.

17. The medical image processing apparatus according to claim 1, wherein the processing circuitry is configured to reset the weighting factor to a weighting factor pertaining to an area or volume of perfusion by the coronary artery.

18. A medical image processing apparatus comprising:

processing circuitry configured to:

acquire a first parameter pertaining to a fractional flow reserve of a coronary artery of a subject and a second parameter pertaining to a myocardium or a pulsation of the myocardium of the subject;

set a weighting factor for the coronary artery, wherein a heavier value is set for the weighting factor at a proximal side than the weighting factor at a distal side; and calculate, based on the first parameter, the second parameter, and the weighting factor, an index pertaining to a condition of the subject.

19. A medical image processing method comprising:

acquiring a first parameter pertaining to a fractional flow reserve of a coronary artery of a subject and a second parameter pertaining to at least one of a shape, character, and fluid resistance related to the coronary artery;

set a weighting factor for the coronary artery, wherein a heavier value is set for the weighting factor at a proximal side than the weighting factor at a distal side; and calculating, based on the first parameter, the second parameter, and the weighting factor, an index pertaining to a condition of the subject.

* * * * *